United States Patent [19]

Ronemus et al.

[11] 4,453,414
[45] Jun. 12, 1984

[54] PULL TESTING ELECTRICAL DEVICE LEADS

[75] Inventors: James R. Ronemus, Lehighton; Lowell Sentman, Catasauqua; William R. Wanesky, Wescosville, all of Pa.

[73] Assignee: AT&T Technologies, Inc., New York, N.Y.

[21] Appl. No.: 384,446

[22] Filed: Jun. 3, 1982

[51] Int. Cl.³ ............................................. G01N 3/08
[52] U.S. Cl. ................................................... 73/827
[58] Field of Search ..................... 73/827, 842; 177/50

[56] References Cited

U.S. PATENT DOCUMENTS

| | | | |
|---|---|---|---|
| 670,296 | 3/1901 | Richardson | 177/246 |
| 3,564,911 | 2/1971 | Slemmons et al. | 73/827 |
| 3,572,108 | 3/1971 | McShane et al. | 73/827 |
| 3,678,740 | 7/1972 | Schmid et al. | 73/827 |
| 3,786,885 | 1/1974 | Mills | 177/245 |
| 3,793,880 | 2/1974 | Sugi et al. | 73/811 |
| 4,282,759 | 8/1981 | Merrell | 73/827 |
| 4,292,852 | 10/1981 | Morris | 73/827 |

Primary Examiner—Anthony V. Ciarlante
Attorney, Agent, or Firm—W. O. Schellin

[57] ABSTRACT

The bond strength of electrical leads (12) bonded to a device (13), such as a silicon integrated circuit chip, is tested by mounting the device (13) onto a pedestal (22) and then pulling on such lead with a freely manipulatable grasping tool (52). The pedestal (22) is coupled to a load sensitive mechanism, such as a simple balance arm (19), or a movable element (21) coupled to a load cell (56). Such mechanism is adjusted to register that part of the pulling force exerted by the grasping tool (52), which is transmitted through the interface between the lead (12) and the device (13).

12 Claims, 4 Drawing Figures

PULL TESTING ELECTRICAL DEVICE LEADS

FIELD OF THE INVENTION

The invention relates generally to pull testing electrical device leads and to apparatus for measuring the strength or quality of a conductive lead to resist becoming separated from its respective electrical device. The invention is particularly useful in determining the bond strengths of leads which are attached to and are the lead-out connections of semiconductive integrated circuit chips.

BACKGROUND OF THE INVENTION

The final assembly of semiconductive devices or chips to form electronic components is uniquely distinct from preceding wafer processing steps in that in the final assembly, operations are typically performed on individual units rather than simultaneously on a large number of units in a batch processing mode. Thus, in final assembly operations, or packaging operations, as they are often referred to, a large number of repetitive and mostly mechanical assembly operations can easily degrade in quality to render a significant portion of the end product, the electronic components, defective. A continuous quality surveillance effort appears to be in order.

Inspection of, for example, electronic components such as semiconductor packages, or any of their subassemblies, is encumbered by their small size with respect to what is typically perceived by the human eye. Microscopes and microscopic images on video screens are typically employed in the inspection of electronic devices or small electrical devices in general to aid the human operator.

A particular failure mode in small electrical device assemblies relates to bonded interconnections between the devices themselves and a lead, or leads, which couple terminals of such devices to external connections. Often an interconnecting contact between a lead and a device is established electrically, but is of insufficient strength to endure a plastic molding operation or to remain intact after temperature cycling. Thus, a device may pass an electrical test prior to plastic encapsulation, but fail electrically after being plastic encapsulated, where the plastic flow in the mold forming the final housing or package has pulled away a lead from the device. The resulting damage may be even more aggravating when the separation of a lead from the device is only partial, so that an electrical failure of the final component is not immediately detected or does not occur until the device is installed in a large piece of apparatus which has been placed into operation.

Testing of the bond strength of leads to small devices prior to such devices becoming packaged, either by plastic encapsulation, or by other means, is therefore particularly important when the manufacture of components of high integrity is desired. However, even though such testing occurs on articles of comparatively very small size, strength test costs are desirably minimized, hence any testing is preferably performed quickly to minimize operator time.

Existing commercial lead test apparatus employs a pedestal for mounting a device the leads of which are to be tested. A vertically movable arm which is positioned above the pedestal, supports a clamp. The clamp is functionally attached to a typical transducive weight sensor of the type commonly referred to as a load cell. When the apparatus is operated, a device to be tested is mounted to the pedestal, and a lead, the bond strength of which is to be tested is aligned with the clamp. The clamp is then closed to grasp the lead to be tested. The vertical movement of the arm is thereafter activated to gradually move it away from the device with an ever increasing pulling force on the lead. During this time, the load cell on the arm registers an increasing force which appears on a digital readout of the cell. The test operator observes and records the highest obtained reading on the lead prior to its breakage or separation from the device.

Problems with such test apparatus have been experienced in that in closing the clamp the leads tend to become damaged to cause at times a lead to break before the strength of the bond of the lead to the device is determined. More importantly, however, the testing cycle to test a single lead including repositioning the device to align a lead with the clamp may require between three and four minutes, such that approximately an hour's time is required to test all leads of a typical 16-leaded device.

It is, therefore, desirable to improve available lead strength testing methods and apparatus to furnish current data from statistical samples of tested devices to operators controlling the final assembly of the corresponding devices.

SUMMARY OF THE INVENTION

In accordance with the present invention, a new and improved method of testing the bond strength between a lead and an electrical device includes mounting the device to a pedestal which is coupled to a load sensor. The lead is then pulled from the device by a freely manipulatable grasping tool. A load differential indicated by the load sensor is observed as an indication of the bond strength between the lead and the device.

Apparatus in accordance with this invention includes a support arm which is movable along a predetermined path and to which is mounted a pedestal for supporting a device, the leads of which are to be pull tested. A predetermined bias force resists a movement of the arm such that a movement of the arm registers a predetermined minimum pull strength of the leads.

A preferred embodiment includes means for registering a range of values. A load sensor is mounted in communication with the support arm, such that the support arm exerts a first predetermined force on the load sensor when the device to be tested is mounted to the pedestal. The apparatus further includes a freely manipulatable grasping tool for grasping any predetermined lead extending from the device, and for pulling any such lead in a direction generally coincident with the predetermined direction of movement of the support arm along such path. The thus exerted pulling force is thereby transmitted through the lead, the pedestal and the support arm to the load sensor to effect a change in the first predetermined force exerted on the load sensor. The change in the force exerted on the load sensor equates to the force exerted through the lead.

A particular feature of the invention is embodied in an apparatus wherein an optical system permits visual contact by an operator of device during the manipulation of the tool. The load sensor is coupled to an audible signal to permit the operator to hear whether the pulling force exerted by the manipulating tool exceeds a predetermined minimum acceptable value.

BRIEF DESCRIPTION OF THE DRAWING

The following detailed description of the invention and of a preferred embodiment thereof will be best understood when read in reference to the accompanying drawing, wherein.

DETAILED DESCRIPTION

1. General Considerations

Figure 1:
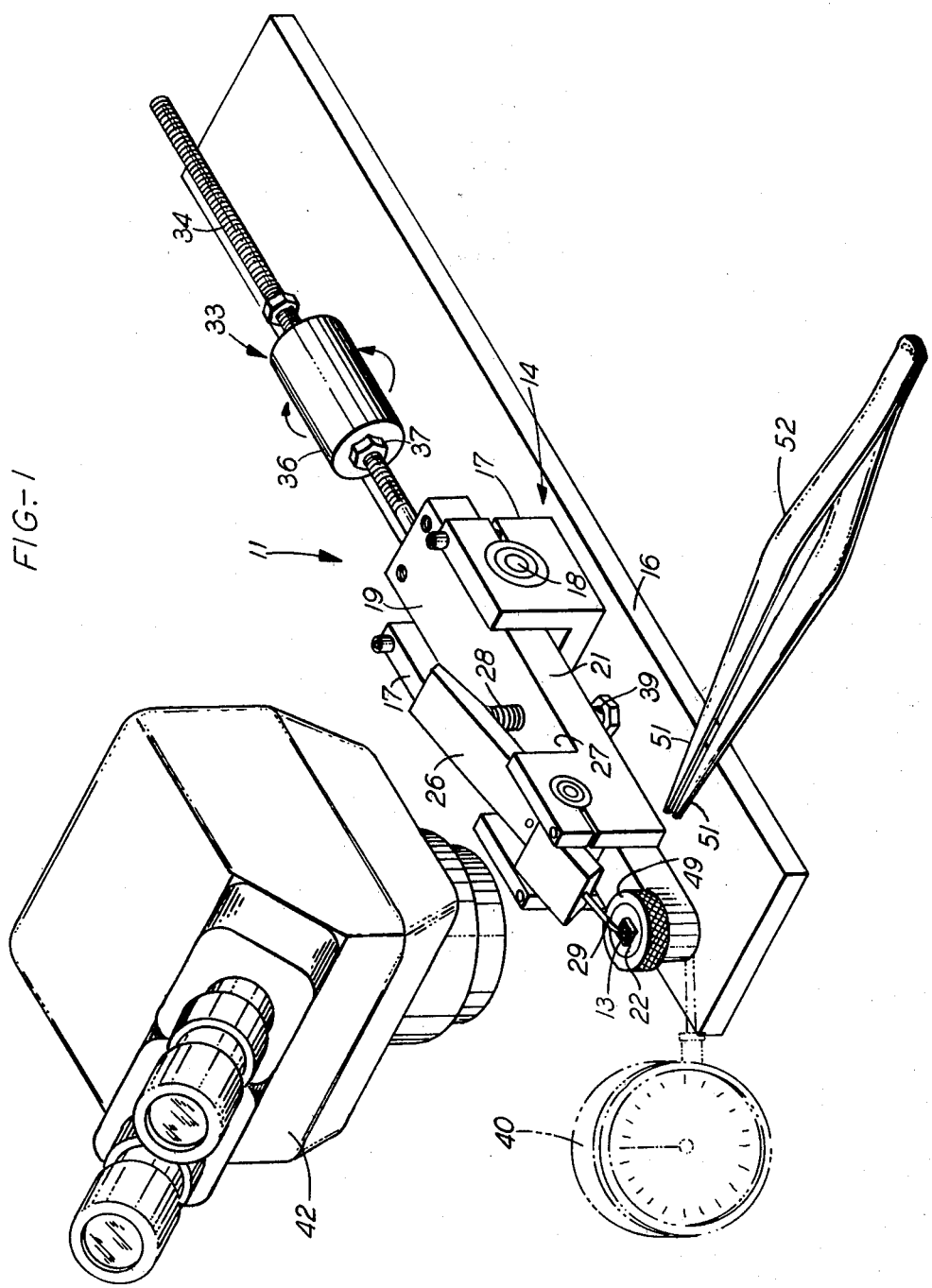
FIG. 1 is a pictorial view of a simple apparatus which embodies features of the present invention.

FIG. 1 is an illustration of apparatus, designated generally by the numeral 11, the structure of which will be useful in describing various features and advantages of the present invention. It should be noted, however, that the following description in reference to the drawing is intended to explain the invention and not to limit it.

The apparatus 11 makes it possible to test the bond strength of conductive leads 12 of a semiconductive or other electrical device 13 (shown best in FIG. 2) which, because of its relatively small size, is preferably tested in accordance with the principles of the present invention. Described generally, the apparatus 11 involves an assemblage of elements which cooperatively interact to indicate to an operator whether the leads 12 bonded to the device 13 meet predetermined bond strength requirements.

It is to be noted that, as in the prior art, the presently described test typically is, and is preferred to be, a destructive test. A destructive test is generally understood to be a test in preparation for which a few samples are selected from a great number of similar items or devices, and the samples are tested in a manner which makes them unfit to be used for the purpose for which they were originally manufactured. Test data gleaned from such destructive tests serve as statistical data to draw conclusions as to whether the remaining devices are acceptable or whether they should be rejected.

Of course, alternatively, the bond strength of leads may be tested on special test leads which are bonded to each device 13 for the sole purpose of inferring therefrom the bond strength of the device leads 12. Since the leads 12 which are necessary to interconnect the device 12 to an external electrical circuit are not affected by testing such special leads, testing such special leads typically would be nondestructive to the device 13. Thus, even though the invention is described with respect to a typically destructive test, its scope extends to such nondestructive testing as well.

Figure 2:
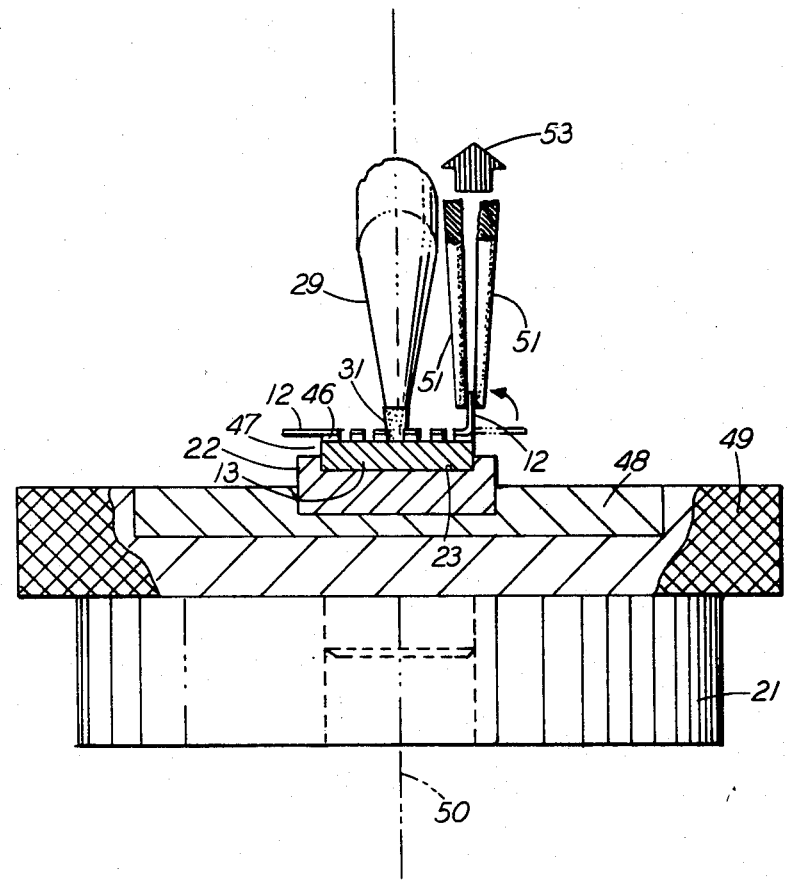
FIG. 2 is an enlarged and partly cut away end view of a balance arm of the apparatus of FIG. 1.

Methods of testing the bond strength between leads 12 and devices 13, as described herein, involve pulling a lead 12 in a direction at substantially right angles to the plane in which the lead 12 is bonded to the device 13. Typically, as shown in FIG. 2, the lead will have to be bent away from its original orientation to point into the direction of the pulling force. Thus, even if the leads 12 of the device 13 under test meet the predetermined bond strength requirements, the leads 12 themselves will have become strained during the test. Returning the leads 12 to their original positions may by itself introduce undesirable defects, such as transverse cracking in the leads. Theoretically, however, it is possible to straighten the leads 12 of a device 13 which has passed the pull test, and to then use the device for its intended purpose.

2. The Apparatus

Of the apparatus 11 shown in FIG. 1, a balance structure 14 is, from the standpoint of physics, in essence a lever of the first kind. A base 16 supports centrally two spaced pillow blocks 17 which pivotally carry a shaft 18 extending transversely to a balance arm 19. The pillow blocks 17 function as fulcrum for the balance arm 19.

In reference to both FIG. 1 and FIG. 2, the balance arm 19 extends to one side of the pillow blocks 17 as a support bar 21 to terminate in a structure supporting an upward facing mounting pedestal 22. The pedestal 22 has a central depression or seat 23 (see FIG. 2) of a predetermined size and shape to accept and locate a device 13, the bond strength of the leads 12 of which is to be tested. A holding clamp 26 (see FIG. 1) is pivotally mounted to the top surface 27 of the support bar 21. A spring 28 urges an outer clamping end 29 of the clamp 26 toward the depression 23 to clamp the device 13 in place for the desired test. The clamping end 29 of the clamp 26 may feature a resilient, protective tip 31 (see FIG. 2), to avoid damaging the device 13 while in contact therewith, should, for any reason, a nondestructive test be desired.

A counterweight portion 33 of the balance arm 19 extends from the pillow blocks 17 in the direction opposite to that of the support bar 21. The counterweight portion 33 is in the embodiment of FIG. 1 a threaded shaft 34, to which a cylindrical counterweight 36 is coaxially mounted. Preferably, the counterweight 36 is internally threaded concentrically with its cylindrical axis with a slightly oversize thread which permits it to be spun freely along the threaded shaft 34. A hexagonal lock nut 37 which may be mounted on either end of the counterweight 36, or on both sides, as shown in FIG. 1, is then used to lock the counterweight in a desired position on the shaft 34.

A precise desired position of the counterweight 36 may be established by placing a device 13 of the type to be tested on the seat 23 of the pedestal 22. In a normally adjusted rest postion, the support bar 21 rests against a stop 39 with an imbalance of the balance arm 19. To lift the balance arm 19 from the stop 39 desirably requires a force equal to the predetermined minimum acceptable pull strength of the bonds holding the leads to the device 13. The stop 39 is mounted to the base 16 and extends from the base to a preferred height to arrest the downward motion of the support bar 21 when an axis through its centroid is slightly (advantageously between about one and two degrees) below the horizontal. Prior to adjusting the position of the counterweight 36, the lock nuts 37 are turned on the threads of the shaft 34 to space them from the counterweight 36. The counterweight 36 is then rotated about the shaft 34 to adjust the balance of the arm 19. A typical force gauge 40 (shown in phantom lines in FIG. 1) reads a force equal to the minimum acceptable pull strength of the leads 12 (as, for example, 10 grams) when the gauge 40 pushes from underneath against the seat of the pedestal to cause the support bar 21 to start to move away from the stop 39.

Also, to stabilize the pivoting action of the balance arm 19, the centroid of the support bar 21 and the centroid of the counterweight 36 may be offset slightly downward as, for example, by about one degree from a diametrical axis through the fulcrum point of the pillow blocks 17.

After the counterweight 36 has been moved along the threaded shaft 34 to cause the support bar 21 to gently lift from the stop 39 under the upward urging force of the gauge 40 showing the desired reading, such as, for example, 10 grams, the lock nuts 37 are turned on the shaft 34 against the cylindrical bases of the counterweight 36. Care should be taken for the movement of the lock nuts 37 not to disturb the established balance of the balance arm 19. Thus, a final position check of the support bar 21 in relationship to the stop 39 may be desirable after the position of the counterweight 36 has been fixed on the shaft 34. The described off-balance adjustment now necessitates a minimum upward force of, for example, the preset ten grams, to pivot the balance arm 21, from the stop 39. This setting would have been selected as the force equal to the minimum required pull strength of the bonds on the leads 12 to be tested. The balance arm 19, when adjusted to a bias setting as described, becomes an effective load sensor for indicating when a pull on one of the leads 12 has reached the minimum required pull strength.

3. Testing the Leads

The adjustment of the counterweight 36 establishes its correct position for testing any number of devices 13 of the same size, or even of a similar size. Thus once the counterweight 36 has been adjusted, the leads 12 of the devices may be tested.

Figure 4:
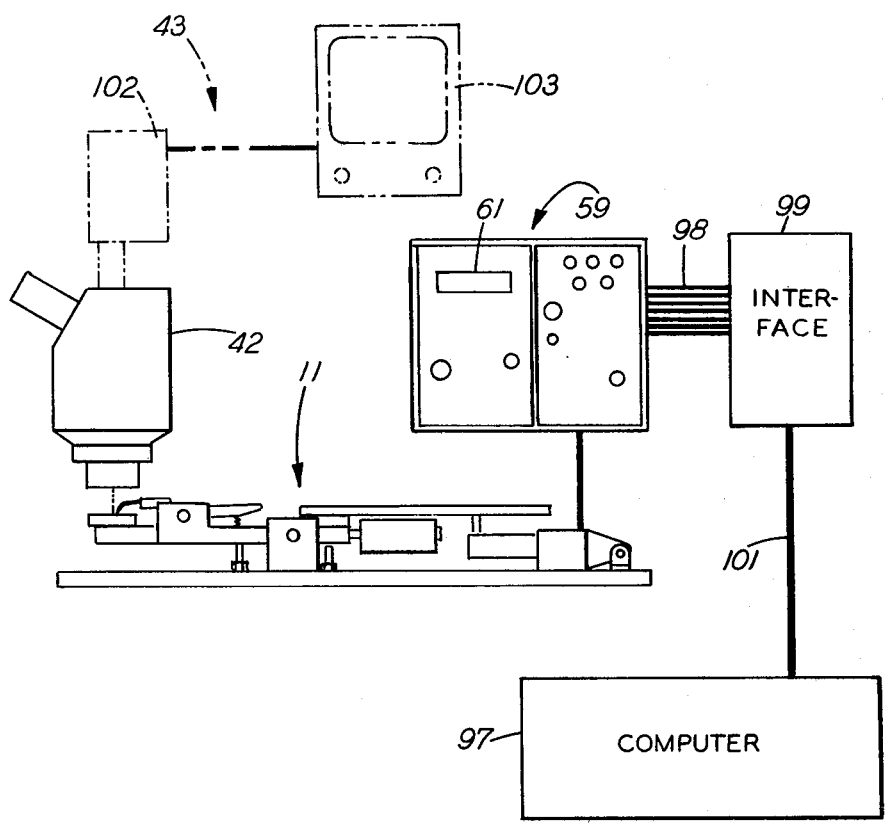
FIG. 4 is a schematic diagram of a data collecting system wherein the present invention is embodied.

At the beginning of a test cycle, an operator raises the end 29 of the clamp 26 and places a device 13 into the seat 23, slowly lowering the end 29 of the clamp 26 against the device to clamp the device 13 against the seat. For loading the device 13 as well as for testing the leads 12, an enlarged image of the device 13 may be viewed through a magnifying optical system such as a typical binocular microscope 42 shown in FIG. 1, or by enlarging video camera and video screen combination 43 as schematically shown in FIG. 4.

To best illustrate testing the leads 12, FIG. 2 shows an enlarged, partially sectioned view of a device 13 loaded into the seat 23. The device 13 is typically of a rectangular or square shape, having a plurality of leads 12 bonded to contact pads 46 about, and just inside of, its edges 47. The leads 12, which typically extend outward from the device 13 are preferably raised by the height of the pedestal 22 above an upper surface 48 of a circular, knurled support platform 49. The support platform 49 is rotatably mounted in the support bar 21 to permit an operator to reposition the leads 12 of the mounted device 13 by rotating the platform 49 about its mounting center 50. After rotating a lead 12 to be tested to an accessible position, such as, for example, shown in FIG. 2, the lead 12 or any subsequent leads 12 to be tested are grasped, one by one, between free ends or jaws 51 of a freely manipulatable grasping tool, such as the tweezers 52 shown in FIG. 1.

It should be realized that the tweezers 52, being directly manipulatable by the operator, avoid painstaking and time consuming alignment operations associated with the referred-to prior art test apparatus. It appears feasible, however, in conjunction with various other features of the present invention, that a partly mechanized lead handling tool (not shown) be substituted for the tweezers 52, as long as such a tool permits ready manipulation by an operator to avoid disadvantages of the prior art.

To test the adhesion of the lead 12 to the device 13, the tweezers 52 are simply pulled in a direction substantially perpendicular to the plane of the respective contact pad 46 on the device 13 in the direction of the arrow 53. If the lead 12 possesses the desired adhesive strength or bond strength to the device, the pulling force transferred through the lead 12, through the bonded interface between the lead 12 and the device 13 lifts the balance arm 19 away from the stop 39 toward the viewing optics. The normal depth perception of the preferably binocular optics permits the ready detection of such movement of the pedestal 22 with the device 13 toward the viewing optics. Any movement of the arm 21 indicates to the operator that the lead has withstood the minimum required pull force.

The operator is now immediately ready to proceed testing the next lead 12 of the same device 13 until all leads thereof have been tested. It is to be noted that in pull testing the various leads 12 about the device 13, the distance of the contact pads 46 from the fulcrum differs. Consequently, the actual force required to tilt the balance arm 19 differs. However, in a practical example, wherein the pedestal 22 is centered on the support bar 21 at a distance of approximately 80mm from the fulcrum, a device size of 2.5mm along each edge yields an error of approximately 1.5% from a nominal value. In the described test, other minor variations in the tested pull force may occur because of the tweezers 52 being manipulated freely by the operator. A pull on the lead 12 which is exerted in a direction other than perpendicular to the plane of the contact pad 46 may possibly result in a bond failure indication whereas the actual bond strength was marginally acceptable. However, inasmuch as any error introduced by an oblique pull seems to alter a test result by approximately the cosine of the angle of declination from the vertical, any possible error from a true reading as a result of a reasonably small angular variation from the vertical would tend to be inconsequential. Also, since the test is intended to be a quality monitoring test, a marginal failure may give an early warning to avoid an assembly problem in the future.

4. Alternate Embodiments

Figure 3:
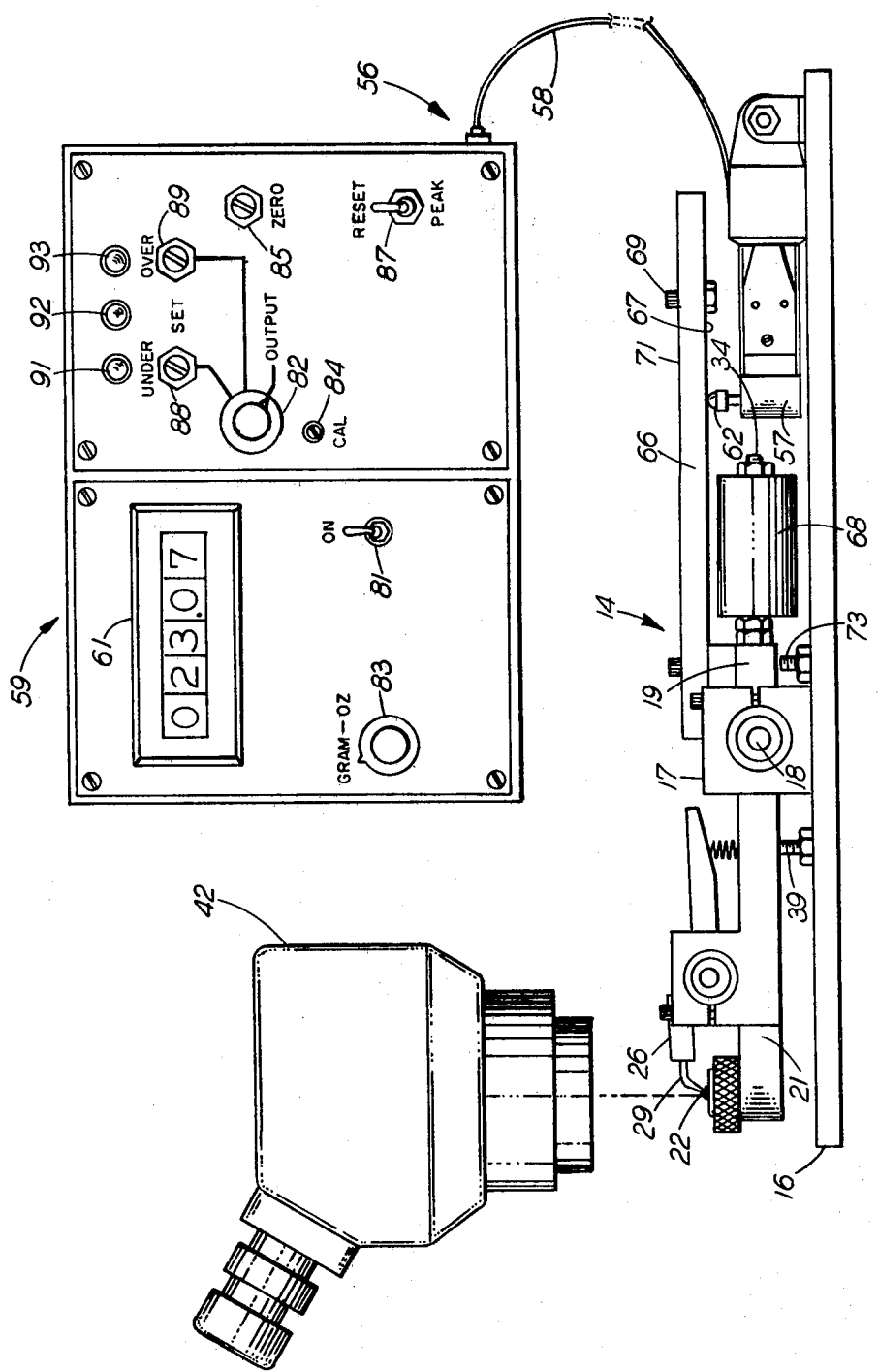
FIG. 3 is a side elevation of an alternate embodiment of the apparatus of FIG. 1 exhibiting preferred features of the present invention.

Various changes and modifications in the apparatus 11 described with respect to FIG. 1 and in the methods of testing described with respect to FIGS. 1 and 2 are, of course, possible. FIG. 3, for example, depicts an alternate embodiment of the apparatus 11 of FIG. 1. A load cell 56 has been added to the balance structure 14. Such a load cell is a transducer apparatus which is commercially available as, for example, from Lion Precision Corp., Newton, Mass. While the load cell 56 may entail intricate electronic circuits, the function of the load cell is readily explained and understood.

The load cell 56 includes a transducer 57, a signal conductor cable 58 and a control console 59 including, typically, a digital readout 61. The transducer 57 includes a force sensitive contact 62 to sense the magnitude of a force and send an electrical signal proportional to such magnitude through the cable 58 to the console 59. The digital readout in response to such signal may be adjusted proportionally to a predetermined standard to achieve a digital readout within a predetermined range of values.

In the embodiment of the apparatus 11, as shown in FIG. 3, the balance arm 19 is further modified to include a counter arm 66 extending from the pillow blocks 17 in a direction opposite to that of the support bar 21. The transducer 57 of the load cell 56 is mounted to the base 16 beneath the counter arm 66, such that a lower surface 67 of the counter arm 66 bears against the contact 62 of the transducer 57. A large counterweight 68 (similar to the counterweight 36) to substantially balance the arm 19 is preferably located below the counter arm 66 on a stub of the threaded shaft 34 to substantially balance the arm 19. An accurate balance adjustment of the arm 19 is preferably obtained by small, slidably mounted counterweights 69 which may be clamped in position on the counter arm at a distance greater than that of the large counterweight 68 from the fulcrum of the balance arm 19

A vertically adjustable safety stop 73 mounted to the base 16 adjacent to the transducer 57 of the load cell 56 arrests excessive downward motion of the counter arm 66 against the contact 62 of the transducer 57. The safety stop 73 thereby protects the transducer 57 from inadvertently becoming damaged by an overload. The height of the contact 62 of the load cell 56 can be adjusted to allow for a small pivotal movement of about one half degree of the balance arm to move from a position wherein the support bar 21 is in contact with the stop 39 to a position wherein the counter arm 66 first touches the contact 62. However, the height of the contact 62 may also be adjusted to a position wherein the contact rests against the counter arm 66 and the support bar 21 on the opposite side of the fulcrum rests against the stop 39. With such an adjustment of the balance arm 19, any movement thereof is directly related to an application of a force on the arm 19, which can be sensed by the transducer 57. An adverse effect of inertia of the balance arm 19 on a force reading is thereby minimized.

The addition of the load cell 56 to the previously described apparatus 11 as shown in FIG. 1 adds the capacity for quantitatively evaluating the lead strength to the existing capability of determining whether a predetermined threshold value is exceeded. The operation of the load cell 56 in conjunction with the balance arm 19 is best described in reference to the features shown on the control console 59 in FIG. 3. For example, in an initial adjustment of the balance arm 19, a light preloading of the cell is desirable. Assuming that the control console 59 is properly connected to a typical electrical alternating current line outlet (not shown), when a power switch 81 is turned on and a selector knob 82 is turned to an output position, the digital readout 61 will display an uncalibrated number in response to a signal from the transducer 57.

Preloading the cell 56 is understood to mean adjusting the balance arm 19, that with the device 13 loaded onto the pedestal 22, a small preloading force of, for example, five grams is exerted against the contact 62. Such preloading force is achieved by observing an initial no-load reading on the digital readout 61 and then adjusting the counterweights 69 outwardly away from the pillow blocks 17 until the number viewed on the digital readout has increased by the desired increment. When a gram-ounce selector switch 83 is set to "gram" as shown in FIG. 3, the initially displayed number should have increased by five units.

Typically the unit is correctly calibrated to read a force in grams exerted downward on the contact 62.

The distance along the balance arm 19 from the center of the pedestal 22 to the fulcrum preferably equals that from the fulcrum (the center of the 18) to the contact 62. Consequently, an upwardly directed pulling force on the pedestal translates to an equal downwardly directed force by the counter arm 66 on the contact 62. A slope calibration, which is accomplished by turning an adjustment screw 84 (identified by "CAL") on the console 59 is typically not necessary.

After the cell 56 is preloaded as described, the readout 61 is adjusted to "zero" by turning an adjustment screw 85 which, on the console 56 in FIG. 3, is labelled as "ZERO." During the described adjustment, a toggle switch 87, which may be toggled between "PEAK" and "RESET" positions, should be placed into the "RESET" position wherein the readout 61 is updated in approximately one-second intervals to a most recent force reading, whether higher or lower. When the switch is in the peak position the highest attained force reading will be locked into a display register and will be displayed by the readout 61.

Turning the selector knob 82 to "SET UNDER" and then to "SET OVER" positions, permits a lower force limit and an upper force limit to be preset by adjusting the adjustment screws 88 and 89 while the knob 82 is in the respective set position. In conjunction with the apparatus and methods described herein, the "UNDER" adjustment is used to preset a lowest acceptable force value. As the screw 88 is turned while the selector knob 82 is in the "UNDER" position, the value displayed by the readout 61 changes correspondingly. When a desired value has been reached, which for purposes of illustration, is 10 grams, for example, the adjustment of the lower acceptable force limit is complete and the selector knob is turned to the "OVER" position.

In the "OVER" position a similar adjustment is performed whereby the adjustment screw 89 is turned to establish an upper marginal force limit. A typical value for the upper marginal force limit is, for example, 20 grams. For example, if a bonded interface separates under an indicated maximum force of less than ten grams, the pull strength test has been failed and tests on additional sample devices 13 become necessary. If the bonded interface of the tested lead 12 fails between 10 and 20 grams, the bond strength is sufficient, but further devices 13 may be tested to accummulate more data and to possibly submit other devices 13 of the same processing lot to temperature cycling tests. If the pulling force at the time of failure of the bonded interface exceeds 20 grams, the test has indicated a solid bond. Whenever the upper limit is reached in consecutive tests, only a minimum number of devices 13 need to be tested for monitoring purposes.

The lower, unacceptable range, the middle, marginal range and the upper range of force values are indicated by light emitting diode (LED) indicators 91, 92, 93, respectively. The LED indicators 91, 92 and 93 are visual alarm indicators which parallel the quatitiative indication of the digital readout 61, when the toggle switch 87 is set into the "peak" position for each pull test. Since the operator will be concentrating visually on the pulling of the lead 12 being tested, the indicator 92 or the indicator 93 may also be preferred to be an audible rather than a visual alarm indicator, such as, for example, an electronic tone generator.

If, for example, the indicator 93 is a tone generator, and the operator performs a pull test with an indication of 23.07 grams, as shown in FIG. 3, the indicator 93 being a tone generator emits an audible tone, indicating to the operator that the range of solid bond values has been reached. Thus, without looking toward the console 59, the operator is able to reset the load cell 56 by the toggle switch 87 or an appropriate foot swithc (not shown), and proceed to test the next lead 12.

Similarly, if the indicator 92 is a tone generator, the sound of the indicator 92 alerts the operator that the lead 12 being tested has reached at least the range of marginal bond strength. When the sound of the indicator 92 ceases while the operator continues to pull on the lead 12 (see also FIG. 2) and the lead has not yet separated from the device 13, the absence of the sound indicates that a bond strength in excess of the predetermined limit of 20 grams is being indicated by the readout 61. Thus, again, without diverting the attention from the microscope 42, the operator can reset the load cell 56 and test the next lead of the device.

FIG. 4 shows a further modification of the apparatus 11, whereby the results obtained from a plurality of lead strength tests are collected by a computer 97 for use in routine statistical evaluations. In FIG. 4, the test result shown on the digital readout 61 of the console 59 is transmitted through, for example, a typical multi-wire cable 98 to an interface unit 99. The interface unit 99 desirably includes a typical register circuit which is directly coupled to what is known as an opto-isolator bank. A timed sampling sequence from the computer 97 through a typical data cable 101 periodically samples the opto-isolator bank. For example, a status signal from one of the opto-isolators the interface unit 99 signals to the computer 97 that a new set of data signals has been stored in the bank of opto-isolators and is ready for transfer to the computer. Upon receipt of such a status signal the computer 97 merely reads the state of the remaining opto-isolators in the bank and stores the obtained data in its memory banks.

Since each test on one of the leads 12 should be preceded by a clearing data of a prior test from the readout 61 of the console 59, the status signal to the computer 97 is desirably generated by the reset pulse from the toggle switch 87 or from any other desirable reset pulse generating switch. The reset pulse however does not reset the data register circuit of the interface unit 99. However, the reset pulse desirably triggers a typical timer circuit of the interface unit 99 which, in turn, resets the data register circuit of the interface unit 99.

FIG. 4 further shows in phantom lines a typical video-imaging system 43, wherein a video camera 102 is coupled to the microscope 42 and transmits image signals of the enlarged view of the pedestal 22 and its surrounding area to a typical video screen 103. Thus, an operator may observe and control the lead pull test by the image on the screen 103.

From the above description of an embodiment of the invention and of its several modifications, it should be understood that further changes and modifications in the apparatus and in the described methods are possible without departing from the spirit and scope of the present invention. For example, a change in the location of the transducer 57 of the load cell 56 to contact the underside of the pedestal 22 is considered to be a modification within the scope of this invention. It should be realized, however, that while such a location of the transducer eliminates the force transmittal of the applied pulling force through the balance arm 19 and the pillow blocks 17, it also requires a sign inversion of the difference in the readout magnitude. As an increasing force is applied to pull the lead 12, the resulting load on the contact 46 decreases and, hence, the value of the readout decreases. Yet, the difference between the starting load on the contact 62 and the final load thereon still represents a measurement of the bond strength of the tested lead 12 to the device 13.

What is claimed is:

1. A method of testing the bond strength of a conductive lead bonded to an electrical device, comprising:
    mounting the device to a pedestal coupled to a load sensor;
    grasping a lead between jaws of a freely manipulatable grasping tool;
    manipulating the tool including the lead in a direction away from the device, and transmitting a force from the tool through the lead and the device, and through the pedestal to the load sensor; and
    observing an indication on the load sensor to determine if the force exceeds a predetermined minimum pull strength required on a bonded interface between the lead being pulled and the device to determine whether the lead has withstood such predetermined minumum pulling force.

2. A method of testing the bond strength of a conductive lead bonded to an electrical device according to claim 1, wherein mounting the device comprises:
    placing the device onto a seat of the pedestal;
    extending the lead beyond the boundaries of the pedestal, such that the lead is raised from an adjacent surface by the height of the pedestal; and
    urging the device into contact with a clamp contacting a central body portion of the device.

3. A method of testing the bond strength of a conductive lead bonded to an electrical device according to claim 1, wherein observing an indication comprises:
    viewing an image of the device and the pedestal mounted to a pivotable arm resting with a predetermined force against a stop; and
    observing whether said arm has moved from its rest position prior to the termination of the test on the lead.

4. A method of testing the bond strength of a conductive lead bonded to an electrical device according to claim 1, further comprising the step of generating an audible alarm signal upon the load sensor sensing a force having a magnitude equal to the minimum required pull strength and wherein the steps of grasping a lead and manipulating include observing an enlarged image of the device, the pedestal, the lead and the jaws, and observing an indication comprises listening for the presence of such audible alarm signal.

5. A method of testing the bond strength of a conductive lead bonded to an electrical device according to claim 1, comprising:
    employing a load sensor capable of producing a continuously variable indication directly proportional to a change in the magnitude of the load on the sensor;
    recording the magnitude of the maximum force transmitted from the tool through the lead and the device to the load sensor; and
    continuing to manipulate the tool until the lead separates from the device; and wherein
    observing an indication on the load sensor comprises comparing said the indication of the maximum transmitted force to an indication of the minimum required pull strength.

6. A method of testing the bond strength of a conductive lead bonded to an electrical device according to claim 5, wherein the continuously variable indication of the load sensor is converted to an incrementally variable indication and the incrementally variable indication is displayed on a digital readout.

7. Apparatus for pull testing the strength of a bond of a lead bonded to an electrical device, comprising:
   a balance arm pivotably mounted to a base;
   means for mounting the device to one side of the balance arm;
   means for retaining the mounted device in its mounted position against an upward directed pulling force on at least one of its leads such that such force is transmitted through the device to the balance arm, such force tending to raise the one side of the balance arm with the means for mounting the device;
   means, mounted to the base in the path of the arm, for resisting a pivotal movement of the arm tending to lower said side of the arm;
   means for biasing the arm with a predetermined biasing force into a position contact with the resisting means; and
   means for indicating when a force of a predetermined magnitude greater than the biasing force tends to move the arm from the preestablished position in contact with the resisting means.

8. Apparatus for pull testing the strength of a bond of a lead bonded to an electrical device according to claim 7, wherein the resisting means is a stop, the balancing means is a counterweight movably mounted on the arm, and the indicating means for visually perceiving an image of the position of the arm is a microscope, whereby a movement of the arm out of contact with the stop may be observed.

9. Apparatus for pull testing the strength of a bond of a lead bonded to an electrical device according to claim 7, wherein the resisting means is a transducer of a load cell, including a contact mounted in the path of the arm, and the indicating means are indicators coupled to a control module of the load cell.

10. Apparatus for pull testing the strength of a bond of a lead according to claim 9, wherein the control module of the load cell further comprises means for generating incrementally varying data which vary proportionally to a change in a bias force on the balance arm.

11. Apparatus for pull testing the strength of a bond of a lead according to claim 10, the apparatus further comprising means which is freely manipulatable with respect to the arm for grasping a lead extending from the device and for pulling it in a direction of the movement of the arm; and means for generating an enlarged image of the device, of the lead and of the grasping and pulling means for permitting an operator to control the relative position of the grasping and pulling means with respect to the device and the lead.

12. Apparatus for pull testing the strength of a bond of a lead according to claim 11, further comprising means for collecting data from a sequence of tests, coupled to the control module of the load cell.

* * * * *

UNITED STATES PATENT AND TRADEMARK OFFICE
CERTIFICATE OF CORRECTION

PATENT NO. : 4,453,414
DATED : June 12, 1984
INVENTOR(S) : J. R. Ronemus, L. Sentman, W. R. Wanesky It is certified that error appears in the above—identified patent and that said Letters Patent is hereby corrected as shown below:

Column 4, line 46, "postion" should read --position--.
Column 8, line 59, "quatitiative"' should read --quantitative--.
Column 9, line 6, "swithc" should read --switch--. Column 9, line 32, after "opto-isolators" insert --of--. In the claims, Column 10, claim 5, line 66, delete --said--. Column 11, claim 7, line 21, "lower said side of the arm" should read --lower said one side of the arm--.

Signed and Sealed this

Twelfth Day of March 1985

[SEAL]

Attest:

DONALD J. QUIGG

Attesting Officer          Acting Commissioner of Patents and Trademarks